(12) United States Patent
Bryntesson et al.

(10) Patent No.: US 7,901,581 B2
(45) Date of Patent: Mar. 8, 2011

(54) CHROMATOGRAPHY METHOD

(75) Inventors: Mattias Bryntesson, Uppsala (SE); Martin Hall, Uppsala (SE); Karol Lacki, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 12/602,774

(22) PCT Filed: Jun. 12, 2008

(86) PCT No.: PCT/SE2008/000393
§ 371 (c)(1),
(2), (4) Date: Dec. 3, 2009

(87) PCT Pub. No.: WO2008/153472
PCT Pub. Date: Dec. 18, 2008

(65) Prior Publication Data
US 2010/0176058 A1     Jul. 15, 2010

(30) Foreign Application Priority Data
Jun. 15, 2007   (SE) .................................. 0701522

(51) Int. Cl.
*B01D 15/08* (2006.01)
(52) U.S. Cl. ....... 210/659; 210/656; 210/673; 210/198.2
(58) Field of Classification Search .................. 210/635, 210/656, 659, 662, 673, 674, 198.2
See application file for complete search history.

(56) References Cited

U.S. PATENT DOCUMENTS

| | | | |
|---|---|---|---|
| 3,291,726 A | 12/1966 | Broughton | |
| 5,457,260 A | 10/1995 | Holt | |
| 5,630,943 A | 5/1997 | Grill | |
| 6,325,940 B1 * | 12/2001 | Ikeda | 210/659 |
| 6,652,755 B2 * | 11/2003 | Ikeda | 210/662 |
| 7,141,172 B2 | 11/2006 | Wang et al. | |
| 2002/0108905 A1 * | 8/2002 | Ikeda | 210/634 |
| 2004/0129137 A1 | 7/2004 | Chin et al. | |
| 2007/0215534 A1 * | 9/2007 | Thommes et al. | 210/198.2 |
| 2010/0176058 A1 * | 7/2010 | Bryntesson et al. | 210/659 |

FOREIGN PATENT DOCUMENTS

| | | |
|---|---|---|
| EP | 1 003 036 | 5/2000 |
| EP | 1 336 610 | 8/2003 |
| EP | 1 733 774 | 3/2010 |
| WO | WO 2004/018072 | 3/2004 |
| WO | WO 2004/024284 | 3/2004 |
| WO | WO 2006/116886 | 11/2006 |

OTHER PUBLICATIONS

Bisschops, M. et al., "Simulated Moving Bed Technology in Biopharmaceutical Processing", Recovery Biological Products XI, (2003) Banff, Alberta, Canada). Heeter, G., et al., Journal of Chromatography A, 711:3-21 (1995).
Lacki, K., et al., "Protein A Counter-Current Chromatography for Continuous Antibody Purification", ACS (2004) Anaheim, CA USA.

\* cited by examiner

*Primary Examiner* — Ernest G Therkorn
(74) *Attorney, Agent, or Firm* — Yonggang Ji

(57) ABSTRACT

The present invention relates to a simulated moving bed process, wherein at least one adsorbent is washed after binding of target compound and wherein the outlet of wash liquid from the adsorbent is subsequently passed onto another adsorbent for binding of target compound removed by the washing. In one embodiment, the method comprises binding of at least one target compound using three or more adsorbents connected in series and elution of target compound from said three adsorbents. After the binding to an adsorbent, wash liquid is passed across the adsorbent to recover desorbed and/or unbound target compound, and the outlet of such wash liquid is directed to the adsorbent after the next in the series, to which no feed has yet been added. The target compound is recovered by eluting target compound from the washed adsorbents.

8 Claims, 6 Drawing Sheets

Feed                                    Wash Buffer

Feed                                    Regeneration
                                        Buffer

CHROMATOGRAPHY METHOD

CROSS-REFERENCE TO RELATED APPLICATIONS

This application is a filing under 35 U.S.C. §371 and claims priority to international patent application number PCT/SE2008/000393 filed Jun. 12, 2008, published on Dec. 18, 2008, as WO 2008/153472, which claims priority to patent application number 0701522-5 filed in Sweden on Jun. 15, 2007.

FIELD OF THE INVENTION

The present invention relates to chromatography, and more specifically to process economy and capacity improvement in continuous chromatographic methods. The invention encompasses a method of separating a target compound using semi-continuous chromatography, as well as a system for carrying out such a method.

BACKGROUND OF THE INVENTION

In the biopharmaceutical field, recent advancements in genetic engineering and cell culture technology have driven expression levels higher than ever, putting a considerable burden on down-stream purification, especially the capture step. While the introduction of new chromatography resins significantly improves the efficiency of a process based on a conventional fixed bed chromatography, additional gains can be achieved by operating in a continuous manner. The latter is especially appealing when continuous bioreactors, such as those operated in perfusion mode, are employed.

In continuous chromatography, several identical columns are connected in an arrangement that allows columns to be operated in series and/or in parallel, depending on the method requirements. Thus, all columns can be run in principle simultaneously, but slightly shifted in method steps. The procedure can be repeated, so that each column is loaded, eluted, and regenerated several times in the process. Compared to 'conventional' chromatography, wherein a single chromatography cycle is based on several consecutive steps, such as loading, wash, elution and regeneration, in continuous chromatography based on multiple identical columns all these steps occur simultaneously but on different columns each. Continuous chromatography operation results in a better utilization of chromatography resin, reduced processing time and reduced buffer requirements, all of which benefits process economy. Continuous chromatography is sometimes denoted simulated moving bed (SMB) chromatography.

Bisschops et al ("Simulated Moving Bed technology in Biopharmaceutical Processing", Bisschops, M. and Pennings, M., Recovery Biological Products XI, (2003) Banff, Alberta, Canada) discloses a continuous chromatography method based on simulated moving bed (SMB) technology, which has been successfully employed for the laboratory scale purification of IgG with a protein A affinity resin. Despite the fact that the multi-column and multi-zone continuous approach provided by SMB greatly increases process efficiency, SMB systems have not been utilized to date for cGMP biopharmaceutical production, mainly because of system complexity from both hardware and operational perspectives.

Heeter et al (Heeter, G. A. and Liapis, A. I., J. Chrom A, 711 (1995)) has suggested, as an alternative to a typical four zone SMB system, a method based on a three column periodic counter-current chromatography (3C-PCC) principle. More recently, Lacki et al ("Protein A Counter-Current Chromatography for Continuous Antibody Purification", Lacki, K. M. and Bryntesson, L. M., ACS (2004) Anaheim, Calif. USA) described the use of such a 3C-PCC system for IgG adsorption to MABSELECT™ affinity resin. This 3C-PCC method requires simpler hardware and easier operation than the typical four zone SMB system, directly reducing the cost associated with the capital equipment and the maintenance of the system.

In fact, simulated moving bed technology has been utilised for decades in various other fields. For example, U.S. Pat. No. 3,291,726 (Universal Oil Products) described as early as 1966 a continuous simulated counter-current sorption process for the petrochemical industry.

U.S. Pat. No. 6,325,940 (Daicel) relates to a simulated moving bed chromatographic system comprising packed beds filled with separating fillers, by which the separation performance of the packed beds can be evaluated without removing the packed beds from the circular fluid passage. As the packed beds can be evaluated without removal thereof, the system can be examined on whether the deterioration of the system is caused by the columns or not, and, if yes, which column causes the deterioration. The system comprises at least four packed beds connected in series and endlessly to each other and ports for adding and taking out fluid.

U.S. Pat. No. 5,457,260 (UOP Inc.) relates to a control process for simulated moving adsorbent bed separations. More specifically, a process of continuously controlling at least one characteristic of a simulated moving adsorbent bed separation process is disclosed. The characteristics controlled may be the purity or the recovery of the component of interest. The process involves measuring the concentration of the components in the pumparound or pusharound stream, calculating the value of the characteristic, and making required adjustments to operating variables according to an algorithm which relates changes in the value of the characteristic to the changes in the concentrations of the components resulting from changes in the operating variables. Thus, the necessary quantity of data to control the separation is rapidly generated, thereby providing efficiency, precision and accuracy.

An essential factor for a reliable continuous process is the quality of the columns used, and more specifically the similarity or even identity between columns. If the columns are not identical, the theoretical calculations will not be correct, and it will become difficult to design an efficient and robust continuous chromatography process. Also, for scale-up considerations, having identical columns in the system is essential. However, the packing of a column with a chromatography media is very complex in order to obtain repeatable results. Even small differences in the number of plates or other packing properties can have a huge effect on the end result.

Pre-packed columns for large scale chromatography are available on the market. The advantage of pre-packed columns is that the supplier provides a column already packed with resin to the end user, whereby said user can include the column into a process without having to go through the relatively complex procedure of column packing However, for such columns to be useful in continuous chromatography; they need to be packed within very tight specifications. Such similar columns are available for analytical scale chromatography, and for small scale preparative chromatography. However, for large scale operation, there is still a need of pre-packed chromatography columns, which are provided with suitable means for connection to such a system, which columns are packed within tight specifications.

In the pharmaceutical industry, biomolecules, such as proteins, nucleic acids etc, are commonly separated by conventional chromatography using a single column. However, even though safety and quality issues may be easier controlled in a single column than in a more complex set-up, a common concern is the capacity obtained using such conventional chromatography. Thus, there is a need in this field of improved methods of chromatography, which improve the overall efficiency and economy obtained today with single column chromatography.

BRIEF DESCRIPTION OF THE INVENTION

In one aspect, the present invention provides a novel operational principle for a semi-continuous liquid chromatography system. More specifically, the invention provides an increased throughput of the desired component of components from a fluid mixture, such as a fermentation broth. This may be achieved as defined in the appended claims. In a specific aspect, the invention provides improved chromatographic performance in a method of liquid chromatography which method comprises washing the resin to which at least one target has been bound before the elution step.

In an additional aspect, the present invention provides the use a set of at least three substantially identically packed chromatography columns in a semi-continuous chromatography method according to the invention.

Further aspects and advantages of the invention will appear from the detailed description and examples below.

DEFINITIONS

Figure 1:
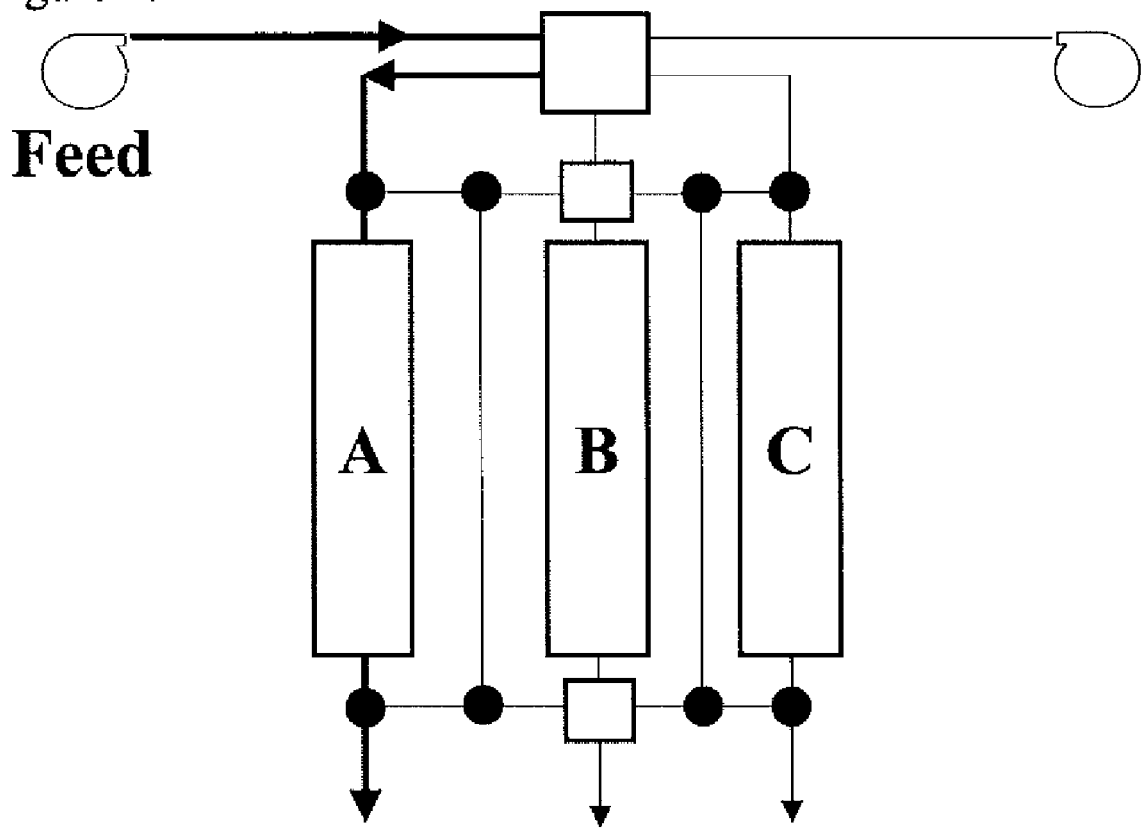
FIG. 1 shows the schematic representation of one embodiment of the invention using a three chromatography column periodic counter current (3C-PCC) system.
Figure 2:
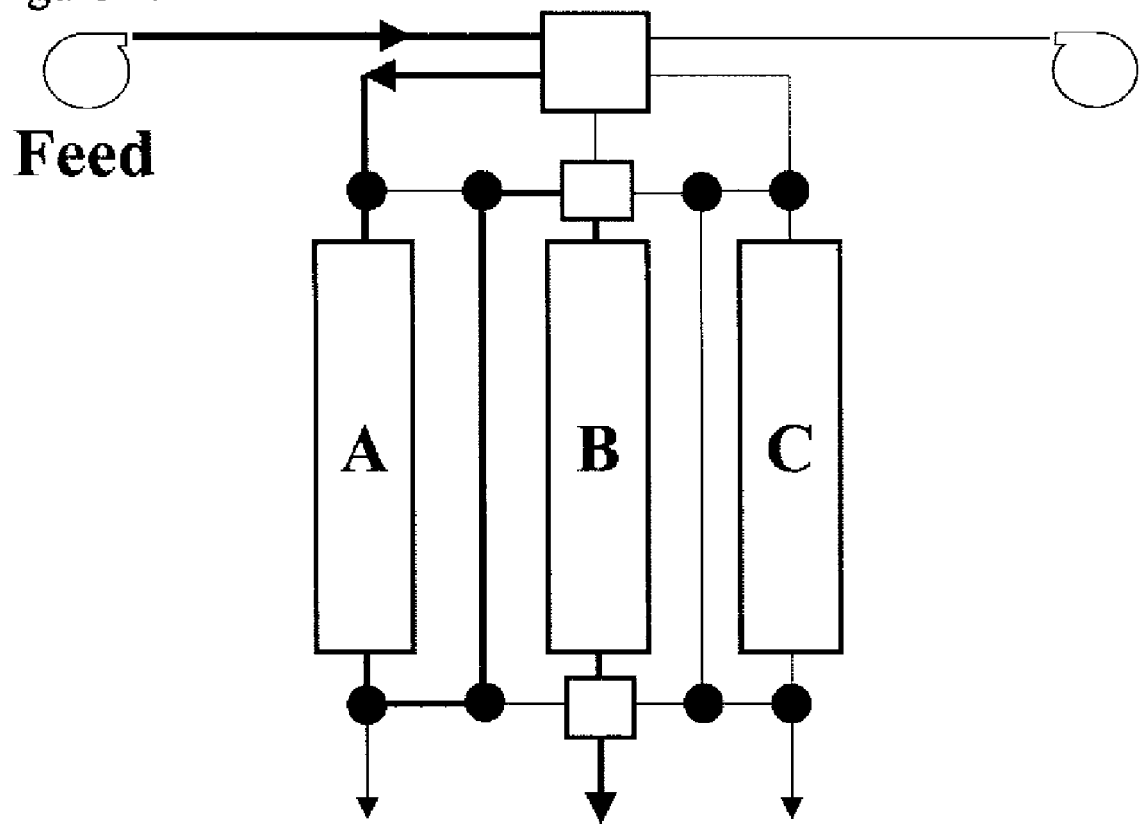
FIG. 2 shows, in the system of FIG. 1, the flow path for the feed solution during the loading of columns 1 and 2 with feed.
Figure 3:
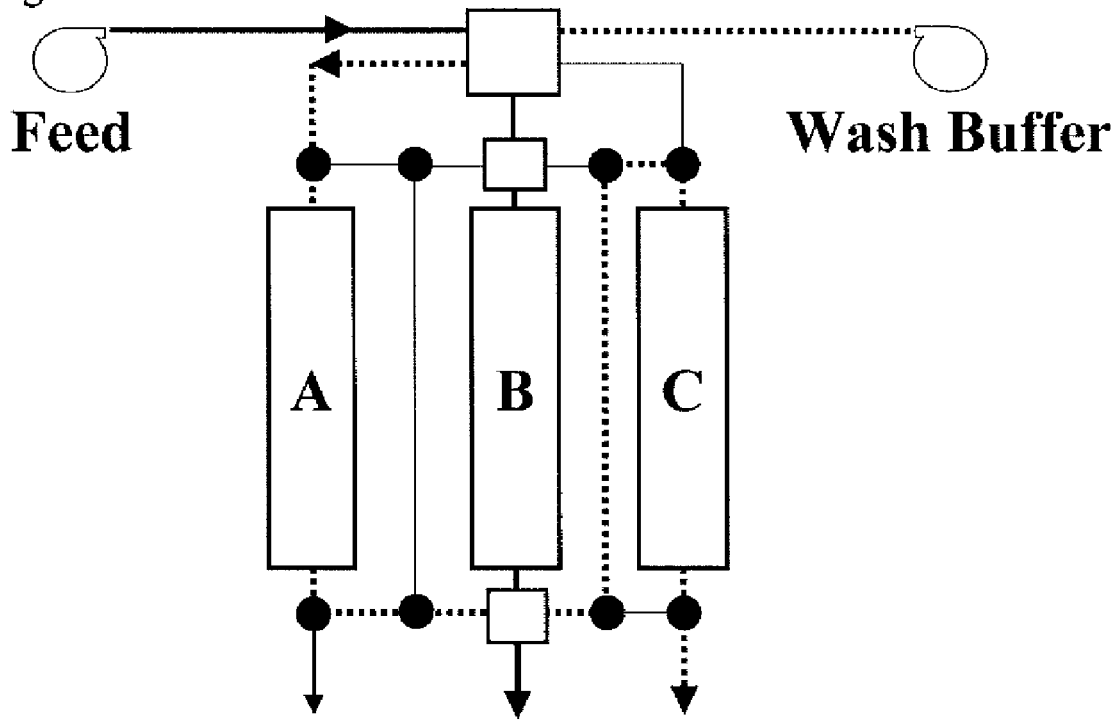
FIG. 3 shows, in the system of FIG. 1, the flow path for the feed and buffer wash during one of the stages during the operation of the 3C-PCC system.
Figure 4:
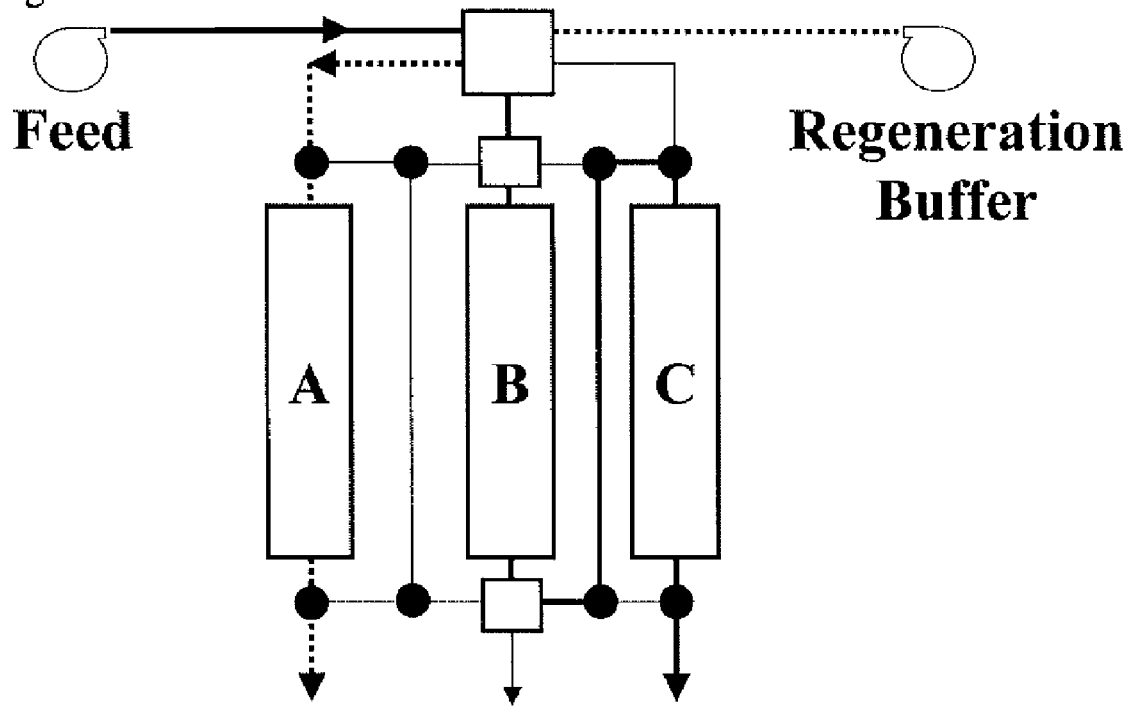
FIG. 4 shows, in the system of FIG. 1, the flow path of for feed and regeneration streams during one of the stages during the operation of 3C-PCC.

The term "feed" refers to a liquid which contains two or more compounds to be separated. In this context, the term "compound" is used in a broad sense for any entity such as a molecule, chemical compound, cell etc.

The term "target compound" means herein any compound which it is desired to separate from a liquid comprising one or more additional compounds. Thus, a "target compound" me be a compound desired e.g. as a drug, diagnostic or vaccine; or, alternatively, a contaminating or undesired compound which should be removed from one or more desired compounds.

The term "break-through" means the point of time during feed addition to an adsorbent such as packed chromatography column when the compound adsorbed first appears in the outflow. In other words, the "break-through" is the point of time when loss of target compound begins.

The term "saturation level" means the point of time when an adsorbent such as a packed chromatography column retains only a part of its original capacity to adsorb a specific target compound.

The term "full saturation" means the point in time when an adsorbent such as a packed chromatography column is not able to adsorb any more of a specific target compound.

The term "regeneration" means herein a process of treating an adsorbent to make it useful again in chromatography. Thus, "regeneration" will include release of bound compounds, also known as elution of compounds, as well as re-equilibration with the appropriate adsorption buffer. As will be discussed below, "regeneration" may also include cleaning in place (CIP).

The term "wash" means herein a process of treating an adsorbent, such as a chromatography column, with a suitable liquid to wash out e.g. one or more target compounds that are not bound, or bound weakly enough to be released from an adsorbent after its saturation to a desired saturation level.

The term "affinity resin" means herein a resin wherein the functional groups of the ligands are capable of binding target compounds via a "lock/key" mechanism, such as antibody/antigen; enzyme/receptor; biotin/avidin; Protein A/antibody etc. Affinity resins are known to bind target compounds with high specificity, and said binding is normally based on more than one kind of interaction. Well known affinity resins are e.g. Protein A coupled to particles, such as Protein A SEPHAROSE™ or PROSEP®-A.

The term "semi-continuous" chromatography system means herein a system for continuous adsorption but discrete elution.

The term "flow programming" means a deliberate change in feed flow rate during application of feed to a chromatography column.

The term "capture" means in the context of a chromatography method the first chromatography step, wherein a large amount of target compound is captured.

DETAILED DESCRIPTION OF THE INVENTION

Thus, in a first aspect, the present invention relates to a method of separating at least one target compound from a feed, which method is a simulated moving bed process wherein at least one adsorbent is washed after binding of target compound and wherein the outlet of wash liquid from said adsorbent is subsequently passed onto another adsorbent for binding of target compound removed by said washing. The adsorbent to which the wash liquid is directed is advantageously a fresh adsorbent, to which no target compound has yet bound. Consequently, every time the feed is redirected to another adsorbent in the system, said adsorbent will have a small amount of target compound bound already. Thus, the present invention allows an efficient recovery of target compound.

One embodiment of the invention is a method of separating at least one target compound from a feed which method comprises continuous binding of at least one target compound to one or more of three or more adsorbents which are connected in series, and discrete elution of target compound from said three adsorbents; wherein after the binding, wash liquid is passed across each adsorbent to recover desorbed and/or unbound target compound, and the outlet of such wash liquid is directed to the adsorbent after the next in the series, wherein said target compound is recovered by eluting target compound from the washed adsorbent. As the skilled person in this field will understand, the last adsorbent of the series will be connected to the first in order to create a cyclic process. As appears from the above, the present system will be operated in series, as the adsorbents are connected to each other so as to allow communication in series, while regeneration of columns most advantageously is carried out essentially simultaneously with feed loading, but in an adsorbent which has temporarily been disconnected from the series.

The adsorbent used in the present method may be a packed bed, such as chromatography resin packed in a column, a membrane, a monolith, a hollow fibre or any other suitable format. In this context, it is understood that the present method is useful with any adsorbent in which a breakthrough curve appears during the application of feed. As the skilled person in this field will understand, to fully benefit from the advantages of the present inventors, the adsorbents should be of the same kind, for example chromatography columns comprising the same kind of packing material. Chromatography resins may e.g. be affinity resins, such as Protein A-based resins; chelating resins known as IMAC resins; hydrophobic interaction chromatography (HIC) resins; thiophilic resins; ion exchange resins, and multimodal resins wherein the ligands comprise two or more functionalities, such as multimodal ion exchangers. The ligands of the chromatography resins may be coupled to particles, such as in resins comprised of very small essentially spherical particles. Membranes may be of any thickness, and includes filters, filter stacks, and other variants, to which binding groups have been coupled. Monoliths are well known in the field of chromatography, and are in principle synthetic polymer plugs, which may be as thin as a membrane or thicker to fill part or all of a chromatography column.

More specifically, in one embodiment, the present method comprises
(a) passing feed comprising at least one target compound across a $1^{st}$ adsorbent, and directing the outflow from the $1^{st}$ adsorbent to a $2^{nd}$ absorbent;
(b) redirecting the feed to the $2^{nd}$ adsorbent, and passing wash liquid across the $1^{st}$ adsorbent to which target compound has bound;
(c) directing the wash liquid outflow to the $3^{rd}$ adsorbent and subsequently directing the outflow from the $2^{nd}$ adsorbent to a $3^{rd}$ adsorbent;
(d) regenerating the $1^{st}$ adsorbent;
(e) redirecting the feed to said $3^{rd}$ adsorbent, and passing wash liquid across the $2^{nd}$ adsorbent to which target compound has bound;
(f) directing the wash liquid outflow to the $1^{st}$ adsorbent, and subsequently directing the outflow from the $3^{rd}$ adsorbent to the $1^{st}$ adsorbent
(g) regenerating the $2^{nd}$ adsorbent;
(h) redirecting the feed to said $1^{st}$ adsorbent, and passing wash liquid across the $3^{rd}$ adsorbent to which target compound has bound;
(i) directing the wash liquid outflow to the $2^{nd}$ adsorbent, and subsequently directing the outflow from the $1^{st}$ adsorbent to the $2^{nd}$ adsorbent
(j) regenerating the $3^{rd}$ adsorbent;
(k) repeating steps (b)-(j);
wherein at least one target compound is collected in step (d), (g) and/or (j).

The feed applied to the adsorbents used in the present method may be any liquid mixture, advantageously a fermentation broth that contains biomolecules expressed by cells. In an alternative embodiment, the feed comprises blood or blood plasma, or some other biological fluid. The feed is advantageously combined with a suitable buffer. Such buffer will be selected dependent on the nature of the target compound, the chromatography resin and other parameters and is adjusted to suitable conditions for binding i.e. adsorption of target compounds.

In one embodiment of the present method, the feed is a fermentation broth or a biological fluid as discussed above, which has been subjected to one or more steps or pre-treatment such as filtration, e.g. to get rid of cell debris, flocculation, sedimentation or chromatography. In an advantageous embodiment of the present invention, the present method is used in a process handling large volumes of liquids, such as the first step of a large scale biopharmaceutical process for the purification of a biomolecule, as discussed below. Even though the invention is equally applicable to small or analytical scale, its advantages in terms of process throughput will be more pronounced the larger the volumes. In one embodiment, the volume of each adsorbent used in the present method is at least 1 liters, such as in the range of 1-100 liters. In another embodiment, each adsorbent is in the range of 1-60 liters, such as about 56 liters, in another embodiment 1-40 liters and in a further embodiment 1-30 liters. In a specific embodiment, the volume of each adsorbent is in the range of 10-20 liters.

The target compounds may e.g. be selected from the group consisting of proteins, such as membrane proteins or antibodies, e.g. monoclonal antibodies, fusion proteins comprising antibody or antibody fragments, such as Fab-fragments, and recombinant proteins; peptides; nucleic acids, such as DNA or RNA, e.g. oligonucleotides, plasmids, or genomic DNA; cells, such as prokaryotic or eukaryotic cells or cell fragments; virus; prions; carbohydrates; lipids etc. In one embodiment, at least one target compound is a desired entity, such as a biopharmaceutical or a drug candidate, a diagnostic molecule or a vaccine. In this embodiment, contaminants will either pass through the adsorbents of the present system; or bind but elute at conditions different from those of the target compound(s).

In an alternative embodiment, at least one target compound is a contaminant, and a desired biopharmaceutical or drug candidate, diagnostic molecule or vaccine remains in the liquid flowing across the adsorbent. This last-mentioned embodiment is known as "flow-through" mode of chromatography. In a specific embodiment of the flow through mode, adsorbents to which contaminants have bound are discarded after a certain number of repetitions of the present method. Such kind of adsorbents is known as disposables, or single-use product, and is especially advantageous for use with high risk contaminants such as prions or virus in processes with a high requirement of purity, such as in the medical field.

In an advantageous embodiment of the present method, once the feed has been applied to a specific adsorbent, the outflow from said adsorbent is advantageously discarded until around the time when target compound begins to exit the adsorbent, known as the breakthrough of the target. Thus, after a suitable period of time, the outflow is directed to the next adsorbent in the series, whereby essential loss of target compound is avoided as it is being captured on the next adsorbent. However, as the skilled person in this field will understand, it is not essential to the present invention to discard any of the outflow. If desired, such as for reasons of limitations in available equipment, the present method may include a direction of outflow to the said column from the start, i.e. without discarding any outflow. The skilled person in this field can easily decide when the breakthrough occurs, and decide whether to direct the flow to the next adsorbent before, at or after the breakthrough. As this redirection of outflow will occur close to the breakthrough, we will sometimes herein refer to it as the "breakthrough redirection point". Detection of target compound may be obtained by any commonly used detection method, such as UV. Detectors will be discussed in more detail below. As is easily understood, detection of breakthrough need not be carried out in every chromatography cycle. Rather, once a process has been optimised, it will be easy to determine the point of time either by volumes of outflow; or simply be measuring the time passed since applying the feed.

However, as is well known, after breakthrough, more time will usually pass before the adsorbent is fully saturated with target compound(s). For process economy reasons, it is most commonly desired to use each adsorbent until its saturation. Thus, a certain period of time will advantageously pass between the above-discussed breakthrough redirection point and the time at which the feed is actually redirected to the next adsorbent of the series. The skilled person can easily decide based on breakthrough curves for the target compound when to redirect the feed to the next column, and decide whether this predetermined point of time, which is sometimes denoted herein the "saturation redirection point", will occur before, at, or after full saturation.

Thus, referring to the repetitive loop of the specific embodiment of the present method, the breakthrough redirection point will occur in steps (b), (e) and (h), while the saturation redirection point will occur in steps (c), (f) and (i).

As is well known in this field, it is often the case that not all the target compound actually binds to the resin, instead some target compound is commonly desorbed from the resin. Most commonly in chromatography, the resin to which target compound has been bound is simply rinsed, and the rinsing liquid is then discarded. Thus, by such conventional operation, a certain amount of target compound will be lost and not recovered. However, in the present method, once the feed has been shifted to the next adsorbent in the series, the previous adsorbent will be available for washing and regeneration. When washing the adsorbent, conditions will be used which provides for most of the target compound to remain bound, but the desorbed and/or unbound target compound will appear in the wash liquid outflow. According to of the present invention, the wash liquid outflow is directed to the adsorbent after the next in the series, in order to capture target compound. Suitable wash liquids such as buffers are easily chosen by the skilled artisan. In one embodiment, at a given moment, the wash liquid outflow and the outflow from the adsorbent receiving the feed at that moment may be applied one after another, or more or less simultaneously. This is easily chosen by flow rate regulation of respective flow rates and by using the appropriate valves. Regulation of the flow rates will be discussed in more detail below.

As appears from the above, once a specific adsorbent has been disconnected from the continuous process cycle, regeneration is conveniently carried out. The regeneration of the washed adsorbent may be accomplished by well known methods and may include commonly used procedures, such as elution; re-equilibration and optionally a more aggressive cleaning between the elution and re-equilibration. Thus, in order to elute the bound target compound(s), a liquid capable of releasing said target compounds—known as an eluent—is added to the adsorbent. This may be achieved by pumping the eluent through the adsorbent, or, alternatively, as a procedure where eluent is first added, then allowed to act and finally removed. In an advantageous embodiment, the eluent is passed across the adsorbent using the inlet and outlet ports used to add and take out feed and wash liquid, fitted with appropriate valves. Elution of bound target compound from an adsorbent may be stepwise or using changing conditions known as gradients, such as conductivity and/or pH gradients. Suitable elution buffers and ways of mixing gradients are well known to the skilled person.

After the elution of target compounds, the adsorbent will commonly need to be re-equilibrated, which reinstates the conditions initially used when the feed was applied, i.e. the conditions during which one or more target compounds may be bound. Re-equilibration is advantageously obtained by passing a suitable buffer across the column.

As mentioned above, the adsorbent may be cleaned between the elution and the re-equilibration, which process is commonly denoted cleaning in place (CIP). Such CIP will use a liquid which is more aggressive than the wash liquid discussed above, and may e.g. be an alkaline solution such as sodium hydroxide. CIP may be carried out after a certain number of adsorption-elution cycles, or, alternatively, if there are reasons to do so it may be performed as an element of each regeneration. How frequent the adsorbent needs CIP is easily decided by the skilled person in this field.

Thus, regeneration should comprise elution followed by re-equilibration. In a one embodiment, in every second, third, fifth, tenth or twentieth cycle, the regeneration also comprises cleaning in place after the elution. In a specific embodiment, every chromatography cycle comprise regeneration including cleaning in place in addition to the elution and re-equilibration.

The cycle of steps (b)-(j) of the present method may be repeated any number of times, such as twice, five times, ten times or twenty times, all dependent on the parameters of the specific process. The skilled person can easily set up a suitable protocol of repeating cycles, including a suitable number of CIP steps, to isolate a given target compound.

In a second aspect, the present invention relates to a liquid chromatography system for separating at least one component from a feed, which system is comprised of at least three adsorbents connected in series, wherein to each adsorbent, means for inlet and outlet of liquid are provided. In an advantageous embodiment, said means for inlet and outlet, respectively, are provided with valve means to allow the addition of two, three or more inlet streams as well as two, three or more outlet streams. The adsorbents may be connected by conventional piping or tubing.

Thus, in one embodiment of the present system, each adsorbent is provided with multiport means at inlet and/or outlet. Such valve means may e.g. be rotary valves, on-off valves, membrane valves, such as membrane block valves, ÄKTAPILOT™ valves (GE Healthcare, Uppsala, Sweden). Valves suitable for use in simulated moving bed chromatography and continuous chromatography processes are well known in this area, see e.g. U.S. Pat. No. 7,141,172 for an extensive discussion thereof.

In a specific embodiment, at its outlet, each adsorbent is provided with means for detection of target compound. Detectors and sensors suitable to this end are well known in this field, such as e.g. detectors of UV absorbance, light scattering, refractive index etc. The system according to the invention may also be provided with adsorbent performance evaluating means.

As appears from the first aspect of the invention, according to the present invention a number of liquid streams may be added to each column; i.e. the feed and the outlet from feed added to an adsorbent, wash liquid, liquid(s) used for regeneration and elution etc. The system according to the invention may be provided with any conventional means for handling the liquid streams.

In an advantageous embodiment, the present invention utilizes liquid flow rate programming to adjust the flow rate of the liquid streams to each other in a desired manner. In one embodiment, the flow rate of one liquid stream such as the feed or the wash liquid is adjusted to enable that the addition of wash liquid outlet to a given adsorbent is finalised before the feed is redirected to said given adsorbent. Thus, in a first embodiment, the flow rate of the wash liquid outlet to an adsorbent is increased. In this embodiment, the flow rate of the feed may remain unchanged. In a second embodiment, the flow rate of the feed is decreased. In this embodiment, the flow rate of the wash liquid outlet may remain unchanged. One advantage of flow programming is that the productivity of each column may be greatly improved.

In a third aspect, the present invention relates to a computer program which provides flow rate control of a semi-continuous chromatography process according to the invention. The program will provide for a mutually adjusted liquid streams, resulting in improved process productivity. Such a program may e.g. be adapted for a method of purification of antibodies or Fab-fragments, wherein the adsorbent comprises Protein A or other affinity ligands. The program may be provided on a suitable carrier, such as a CD or DVD disk, a memory stick or any other commonly used format.

A specific aspect of the invention is a system as discussed above, which has been provided with a computer program according to the invention to provide an automated system for semi-continuous operation with flow rate programming.

In a fourth aspect, the present invention relates to the use of chromatography columns, which have been provided by the supplier packed with chromatography resin, in semi-continuous chromatography, such as flow rate programmed semi-continuous chromatography. In an advantageous embodiment, the chromatography column used in the present aspect presents substantially identical packing properties. In a specific embodiment, the pre-packed chromatography columns are sanitized, which allows use thereof in the preparation of medical and diagnostic products. In another embodiment, the pre-packed chromatography columns have been qualified according to predetermined standards.

The columns used in this aspect may have been packed with any chromatography resin, synthetic based resins, e.g. styrene-DVB, organic polymer-based resins, such as agarose or dextran, or inorganic resins, such as silica. To the resins conventional ligands are advantageously coupled, such as affinity ligands, ion exchange ligands, hydrophobic interaction chromatography (HIC) ligands, chelating ligands, thiophilic ligands or multimodal ligands. The ligands may be selected for their ability to bind a desired target, such as Protein A ligands which binds antibodies, antibody fragments etc; or for their ability to bind one or more contaminants, such as DNA-binding ligands e.g. ion exchange ligands. The columns may be glass or plastic, and are preferably adapted with luers and/or adaptors for connection to a system according to the invention.

The present invention also relates to a set of at least three chromatography columns, which are packed with chromatography resin as discussed above, and which have been qualified according to standards for use in a method according to the present invention.

EXAMPLES

The present example is provided for illustrative purposes only, and should not be construed as limiting the present invention as defined by the appended claims.

Example 1

Figure 5:
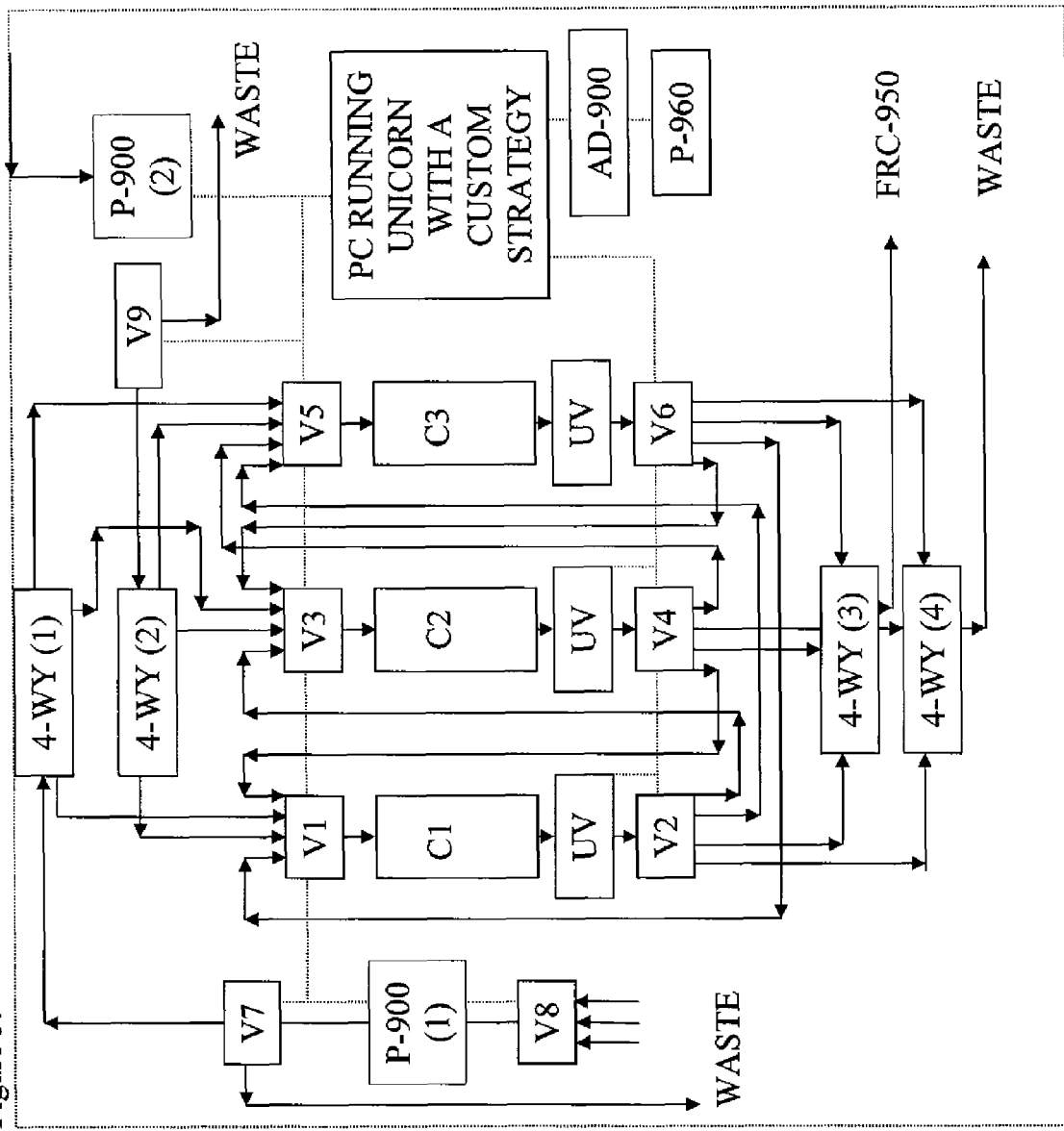
FIG. 5 shows, in the system of FIG. 1, a diagram of the 3C-PCC of the current invention based on the ÄKTAEXPLORER™ platform (GE Healthcare Bio-Sciences, Sweden).

This example illustrates a continuous primary capture step for the purification of human polyclonal IgG on protein A chromatography resin using a three column periodic counter current (3C-PCC) system according to the invention. More specifically, three one milliliters columns (HITRAP™) were packed with the Protein A chromatography resin MABSELECT™ (GE Healthcare Bio-Sciences, Uppsala, Sweden). The columns were connected to a custom modified ÄKTAEXPLORER™ (GE Healthcare Bio-Sciences, Uppsala, Sweden) chromatography system (FIG. 5) that was configured into a three column periodic counter current system, 3C-PCC. The system comprised two independent pumps, 3 UV detectors, pH and conductivity meters, several rotary valves and flow splitters. UV detectors were position such that an effluent from each of the columns was passed through a UV detector. Absorbance from each UV detector and the pH and conductivity levels measured on the waste line were recorded using UNICORN™ software (GE Healthcare Bio-Sciences, Uppsala, Sweden). Eluted from the protein A column hIgG was collected in a single pool.

The following single column chromatography cycle was used as a base for operating the 3C-PCC system in a continuous manner: 1) column equilibration with 3 column volume (CV) of buffer A; 2) column loading with hIgG in buffer A; 3) column wash with 4CV of buffer A; 4) column elution with 4CV of buffer B; 5) column CIP with 4CV of buffer C; and, 6) column regeneration with 3 CV of buffer A. All steps were performed at 0.5 mL/min flow rate giving.

Figure 6:
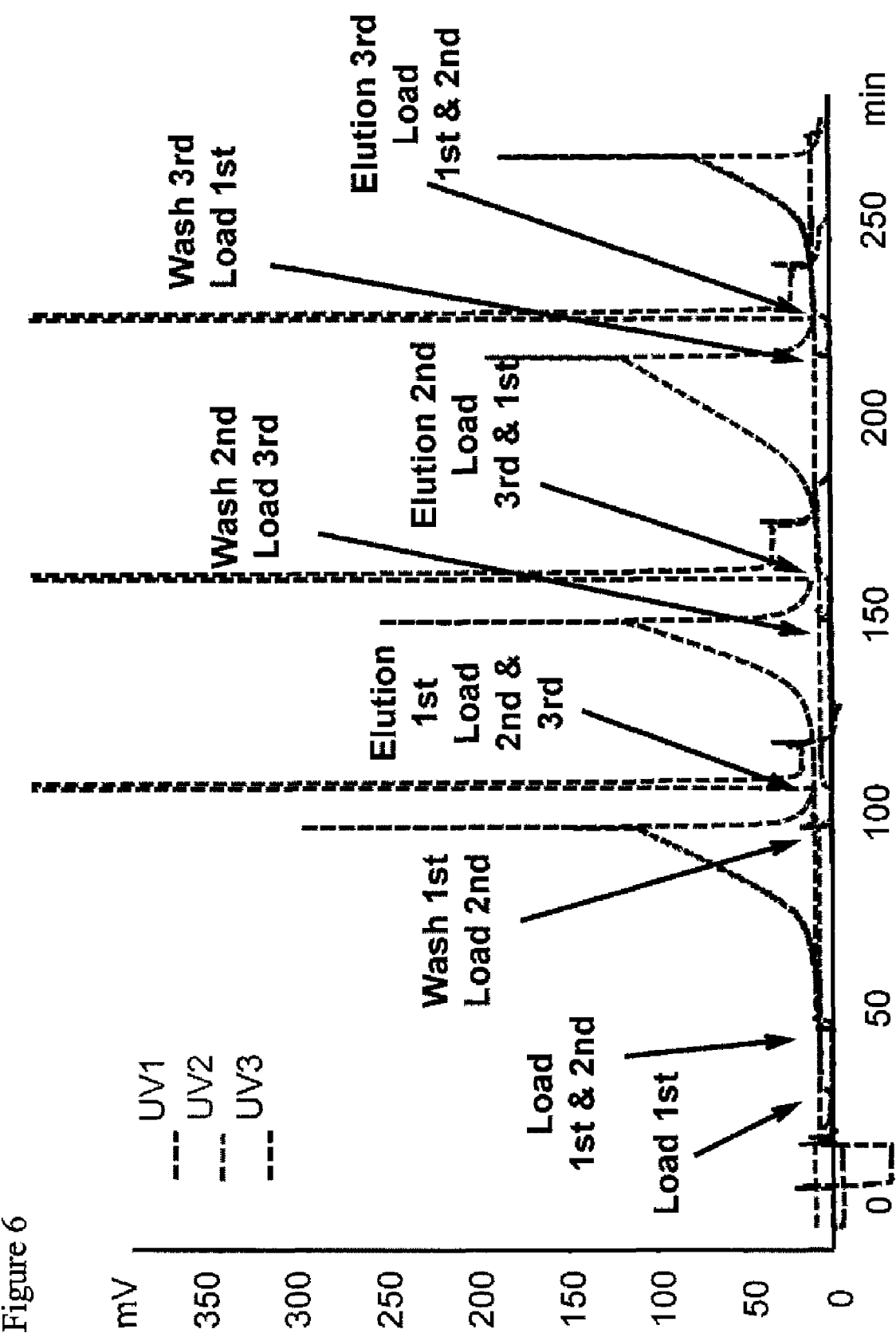
FIG. 6 shows, in the system of FIG. 1, the recorded signals in the effluent streams from all three columns during the start-up cycle of the 3C-PCC system of the invention.
Figure 7:
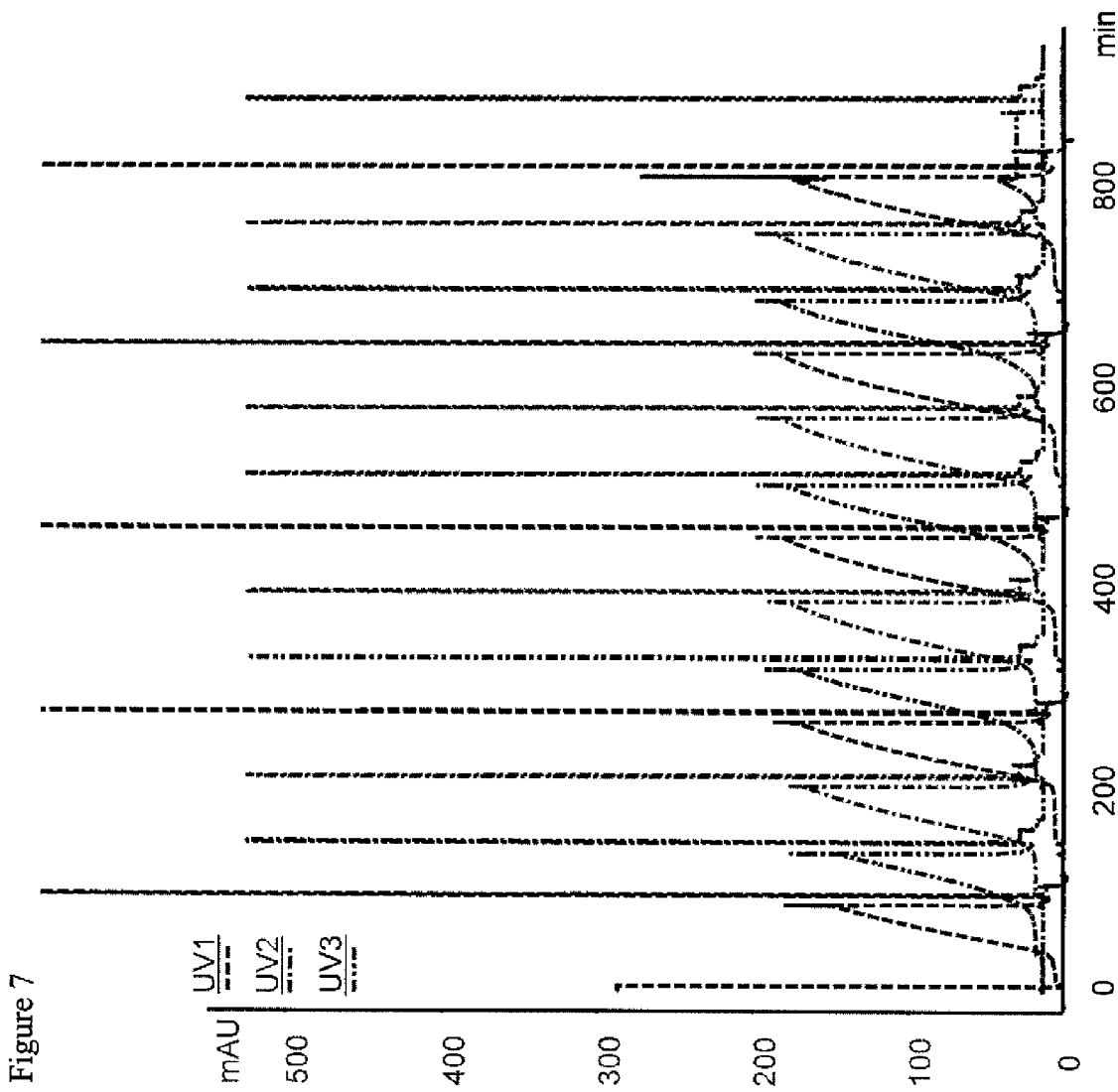
FIG. 7 shows, in the system of FIG. 1, the recorded signals in the effluent streams from all three columns during 4.66 full cycles on the 3C-PCC system of the invention.

Composition of solutions used is given below:
Buffer A: 50 mM Sodium Phosphate, 150 mM NaCl, pH 7
Buffer B: 0.1 M Sodium citrate, pH=3.5
Buffer C: 50 mM NaOH
Feed: 1.65 g/L Polynorm hIgG (Octopharm) dissolved in buffer A Four hundred milliliters of solution containing 1.6 g/L of Polynorm hIgG were continuously fed into the experimental 3C-PCC setup described above. The purified hIgG was eluted from the system in a discreet manner by applying the buffer B into the saturated column. In FIG. 6, signals recorded in the effluent from each of the chromatography column during the first, a start-up, 3C-PCC cycle consisting of: 1) loading of the feed into first column; 2) connecting the $1^{st}$ and the $2^{nd}$ columns in series; 3) directing the feed into $2^{nd}$ column while washing the $1^{st}$ column into the $3^{rd}$ column; 4) connecting the $2^{nd}$ and the $3^{rd}$ columns in series while applying the feed; 5) regenerating the $1^{st}$ column; 6) directing the feed to the $3^{rd}$ column and washing the $2^{nd}$ column in to the $1^{st}$ column; 7) connecting the $3^{rd}$ and the $1^{st}$ columns in series while continuously applying the feed; 8) eluting the $2^{nd}$ column; 9) regenerating the $2^{nd}$ column; 10) directing the feed into the $1^{st}$ column while washing the 3$^{rd}$ column into the 2$^{nd}$ column are shown. The reproducibility of the pattern shown in FIG. 6 is depicted in FIG. 7, where UV signals recorded during 14 single loadings, representing 4.7 3C-PCC cycles, are presented. The chromatograms representing concentration of IgG in effluents from each of the column as shown in FIG. 6 and FIG. 7, are not directly comparable as they recorded using different UV detectors.

Summary of results obtained in this experiment is shown in Table 1 below. These data are compared to the results that would be obtained if a reference run were performed on a single column with the volume equivalent to the total volume of the resin used in the 3C-PCC system.

TABLE 1

Summary of 3C-PCC and a reference single column runs

|  | Single column | 3C-PCC |
|---|---|---|
| Total adsorbent volume (mL) | 3 | 3 × 1 |
| Residence time (min) | 6 | 2 [a] |
| Number of cycles | 7 | 4.7 [b] |
| Buffer requirement (L) | 0.43 | 0.25 |
| Productivity (g/L/h) | 12.3 | 16.5 |

[a] per single column
[b] fourteen single column loadings

Example 2

This example illustrates a continuous primary capture step for the purification of monoclonal antibody (MAb) from a mammalian cell culture supernatant using a three column periodic counter current (3C-PCC) system according to the invention. More specifically, three one milliliters columns (HITRAP™) were packed with MABSELECT SURE™ (GE Healthcare Bio-Sciences, Uppsala, Sweden), and the columns were connected to a custom modified ÄKTAEXPLORER™ (GE Healthcare Bio-Sciences, Uppsala, Sweden) chromatography system essentially as described in example 1 above.

Figure 8:
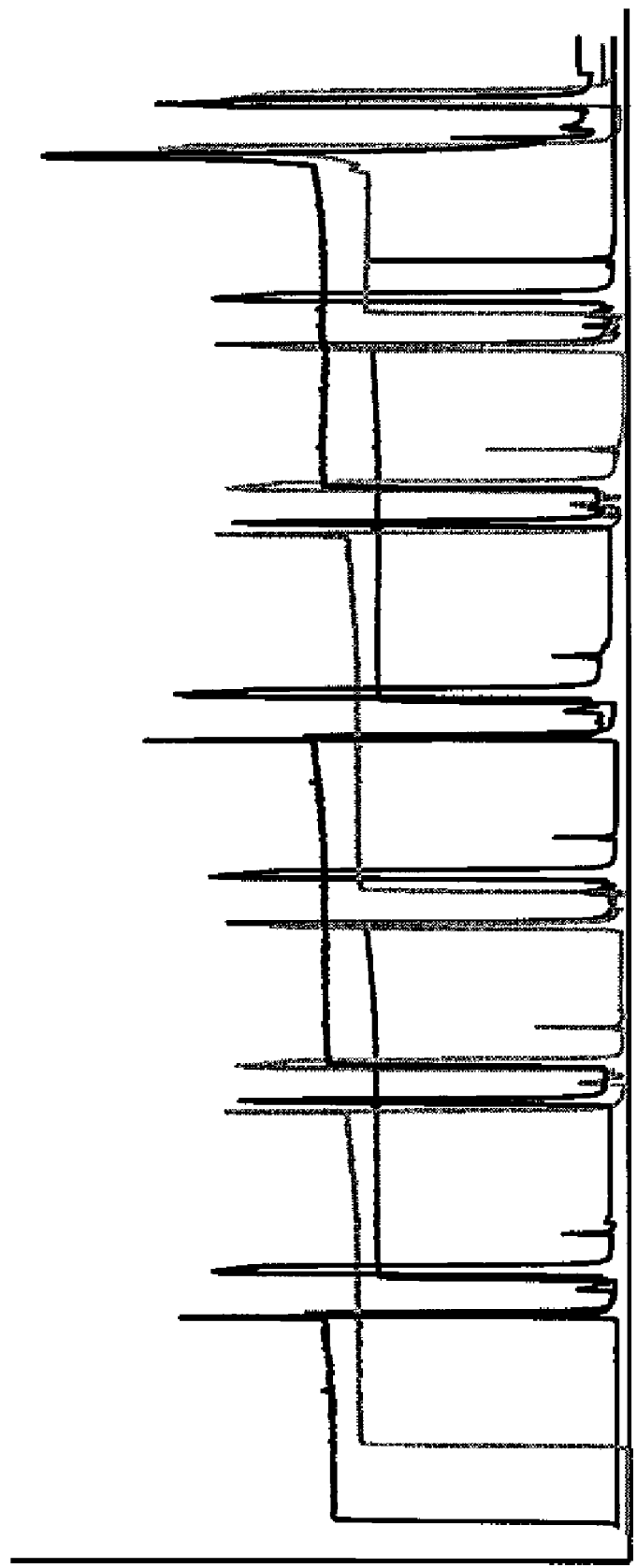
FIG. 8 shows the recorded signals in a chromatogram obtained as described in Example 2. More specifically, this figure shows the results of the purification of a monoclonal antibody from a mammalian cell culture supernatant using a 3C-PCC system according to the invention. The first curve that appears in the chromatograpm (blue curve in original)—column 1, third curve that appears (red curve)—column 2, and the second curve that appears (green curve)—column 3.

In brief, the single column chromatography cycle used as a base for operating the 3C-PCC system in a continuous manner consisted of the following steps: 1) column equilibration; 2) column loading with mAb-containing cell culture supernatant; 3) column wash; 4) column elution; 5) column CIP; and, 6) column regeneration. The chromatogram from the 3C-PCC run is shown in FIG. 8. The concentration of mAb was determined in the eluted fractions, and used for estimation of yield and productivity, see Table 2 below.

TABLE 2

Comparison of 3C-PCC and single column runs.

|  | 3C-PCC | 1 C* |
|---|---|---|
| Columns | 3 × 1 mL | 3 mL |
| Feed | 0.85 g/L | |
| Load | 56 g/L | 35 g/L |
| Time | 16.4 h | 22.4 h |
| Yield | 96% | 90% |
| Productivity | 8 g/Lh | 5.8 g/Lh |

*Results recalculated based on data for 1 mL column

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method of separating at least one target compound from a feed, which method is a simulated moving bed process, said method comprising the steps of:
   washing at least one adsorbent after binding of the target compound;
   subsequently passing the outlet of wash liquid from said adsorbent onto another adsorbent for binding of the target compound removed by said washing; and
   continuously binding at least one target compound to one or more of three or more adsorbents which are connected in series and discrete elution of target compound from said three adsorbents; wherein after the binding, wash liquid is passed across each adsorbent to recover desorbed and/or unbound target compound, and the outlet of such wash liquid is directed to the adsorbent after the next in the series, wherein said target compound is recovered by eluting target compound from the washed adsorbents.

2. The method of claim 1, comprising:
   (a) passing feed comprising at least one target compound across a 1$^{st}$ adsorbent, and directing the outflow from the 1$^{st}$ adsorbent to a 2$^{nd}$ adsorbent;
   (b) redirecting the feed to the 2$^{nd}$ adsorbent, and passing wash liquid across the 1$^{st}$ adsorbent to which target compound has bound;
   (c) directing the wash liquid outflow to the 3$^{rd}$ adsorbent and subsequently directing the outflow from the 2$^{nd}$ adsorbent to a 3$^{rd}$ adsorbent;
   (d) regenerating the 1$^{st}$ adsorbent;
   (e) redirecting the feed to said 3$^{rd}$ adsorbent, and passing wash liquid across the 2$^{nd}$ adsorbent to which target compound has bound;
   (f) directing the wash liquid outflow to the 1$^{st}$ adsorbent, and subsequently directing the outflow from the 3$^{rd}$ adsorbent to the 1$^{st}$ adsorbent;
   (g) regenerating the 2$^{nd}$ adsorbent;
   (h) redirecting the feed to said 1$^{st}$ adsorbent, and passing wash liquid across the 3$^{rd}$ adsorbent to which target compound has bound;
   (i) directing the wash liquid outflow to the 2$^{nd}$ adsorbent, and subsequently directing the outflow from the 1$^{st}$ adsorbent to the 2$^{nd}$ adsorbent;
   (j) regenerating the 3$^{rd}$ adsorbent; and
   (k) repeating steps (b)-(j);
   wherein at least one target compound is collected in step (d), (g) and/or (j).

3. The method of claim 2, wherein the redirection of feed is provided by valve means.

4. The method of claim 1, wherein at least one adsorbent is a column packed with chromatography resin and provided with multiport means at inlet and/or outlet.

5. The method of claim 4, wherein the flow rate of the feed is controlled to improve the productivity of each column.

6. The method of claim 5, wherein the flow rate of one or more additional liquid streams are controlled.

7. The method of claim 1, wherein the washing steps are carried out with different buffers.

8. The method of claim 1, wherein each adsorbent is washed by multiple washing steps.

* * * * *